(12) United States Patent
Anwar et al.

(10) Patent No.: US 12,031,904 B2
(45) Date of Patent: Jul. 9, 2024

(54) OPTICAL FLUID ANALYZER

(71) Applicant: Si-Ware Systems, Cairo (EG)

(72) Inventors: Momen Anwar, Cairo (EG); Mohamed H. Al Haron, Cairo (EG); Yasser M. Sabry, Cairo (EG); Mohamed Sakr, Cairo (EG)

(73) Assignee: SI-WARE SYSTEMS, Cairo (EG)

( * ) Notice: Subject to any disclaimer, the term of this patent is extended or adjusted under 35 U.S.C. 154(b) by 46 days.

(21) Appl. No.: 17/839,102

(22) Filed: Jun. 13, 2022

(65) Prior Publication Data

US 2022/0397518 A1 Dec. 15, 2022

Related U.S. Application Data

(60) Provisional application No. 63/210,450, filed on Jun. 14, 2021.

(51) Int. Cl.
*G01N 21/3504* (2014.01)
*G01N 21/35* (2014.01)
*G01N 33/497* (2006.01)

(52) U.S. Cl.
CPC ....... *G01N 21/3504* (2013.01); *G01N 33/497* (2013.01); *G01N 2021/3595* (2013.01);
(Continued)

(58) Field of Classification Search
CPC ............. G01N 21/3504; G01N 33/497; G01N 2021/3595; G01N 2201/0221;
(Continued)

(56) References Cited

U.S. PATENT DOCUMENTS 8,204,565 B2 6/2012 Arnold et al.
2003/0161359 A1* 8/2003 Harding ............. H01S 5/02326
372/19
(Continued)

FOREIGN PATENT DOCUMENTS

WO 2019188304 A1 10/2019

OTHER PUBLICATIONS

Tan, Zong et al. "A gas Fourier transform infrared spectroscopy methodology for the rapid and accurate discrimination of chicken spoilage through volatiles analysis", Flavour and Fragrance Journal, vol. 34, No. 4, (Apr. 24, 2019), pp. 271-279.
(Continued)

*Primary Examiner* — David P Porta
*Assistant Examiner* — Meenakshi S Sahu
(74) *Attorney, Agent, or Firm* — LOZA & LOZA, LLP; Holly L. Rudnick

(57) ABSTRACT

Aspects relate to an optical fluid analyzer including a fluid cell configured to receive a sample fluid. The optical fluid analyzer further includes optical elements configured to seal the fluid cell on opposing sides thereof and to allow input light from a light source to be sent through the fluid cell and output light from the fluid cell to be input to a spectrometer. The optical fluid analyzer further includes a machine learning (ML) engine, such as an artificial intelligence (AI) engine, that is configured to generate a result defining at least one parameter of the fluid based on a spectrum produced by the spectrometer.

19 Claims, 19 Drawing Sheets

(52) U.S. Cl.
CPC ............... *G01N 2201/0221* (2013.01); *G01N 2201/0227* (2013.01); *G01N 2201/127* (2013.01)

(58) Field of Classification Search
CPC ..... G01N 2201/0227; G01N 2201/127; G01N 21/05; G01N 2021/0346; G01N 21/3577; G01N 2201/0636; G01N 2201/0639
See application file for complete search history.

(56) References Cited

U.S. PATENT DOCUMENTS

| | | | |
|---|---|---|---|
| 2015/0103354 A1* | 4/2015 | Saptari | G01N 21/314 356/455 |
| 2018/0059015 A1 | 3/2018 | Li et al. | |
| 2019/0178786 A1 | 6/2019 | Proskurowski et al. | |
| 2020/0393360 A1* | 12/2020 | Proskurowski | G01N 21/01 |

OTHER PUBLICATIONS

Fong, A et al: "Low-Volume Diffuse-Transmittance Fiber-Optic Near-IR Spectrophotometer", Applied Spectroscopy, the Society for Applied Spectroscopy, vol. 49, No. 4, (Apr. 1, 1995), pp. 486-492.
Baum, Marc M et al: "Measurement of acetylene in breath by ultraviolet absorption spectroscopy: Potential for noninvasive cardiac output monitoring", Review of Scientific Instruments, American Institute of Physics, vol. 74, No. 6, (Jun. 1, 2003), pp. 3104-3110.
Riad, Michael M Y R et al. "On the Detection of Volatile Organic Compounds (VOCs) Using Machine Learning and FTIR Spectroscopy for Air Quality Monitoring", 2019 36th National Radio Science Conference (NRSC), IEEE, (Apr. 16, 2019), pp. 386-392.
Gnambodoe-Capo-Chichi, Martine et al. "Monitoring the purification of tobacco smoke in air assisted by ZnO nanowires and using MEMS-FTIR spectrometer for online continuous analysis of volatile organic compounds (VOCs)", SPIE Proceedings, vol. 10914, (Feb. 27, 2019), pp. 109141N-109141N.
Malak, Maurine: "Beyond Interferometers Based on Silicon-Air Bragg Reflectors: Toward On-Chip Optical Microinstruments-A Re", IEEE Journal of Selected Topics in Quantum Electronics, vol. 21, No. 4, (Jul. 1, 2015), pp. 1-12.
Yu, et al. "Micromachined Fourier transform spectrometer on silicon optical bench platform", Sensors and Actuators A: Physical, vol. 130-131, (Aug. 14, 2006), pp. 523-530.
Hu, Zhixiong et al. "Adapted AWG design for localised spectroscopic measurements", 2013 Conference on Lasers & Electro-Optics Europe & International Quantum Electronics Conference CLEO Europe/IQEC, IEEE, (May 12, 2013), p. 1.
International Search Report & Written Opinion, PCT/US2022/033435, dated Sep. 27, 2022.

* cited by examiner

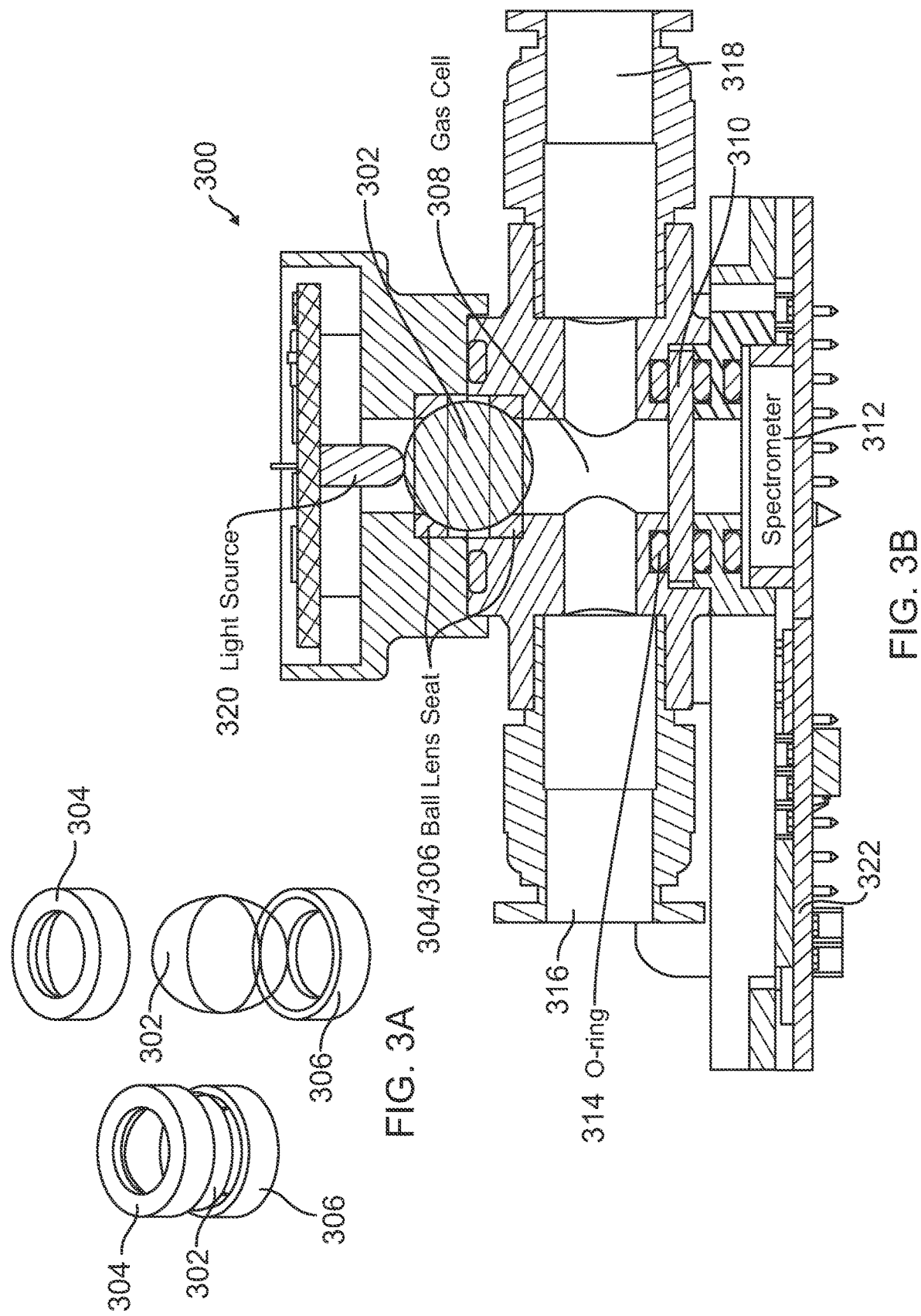

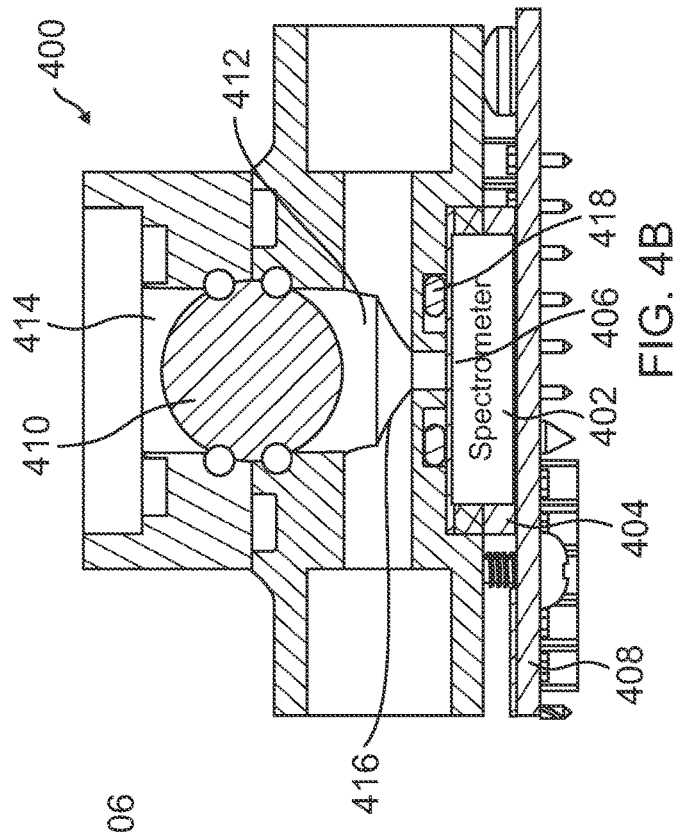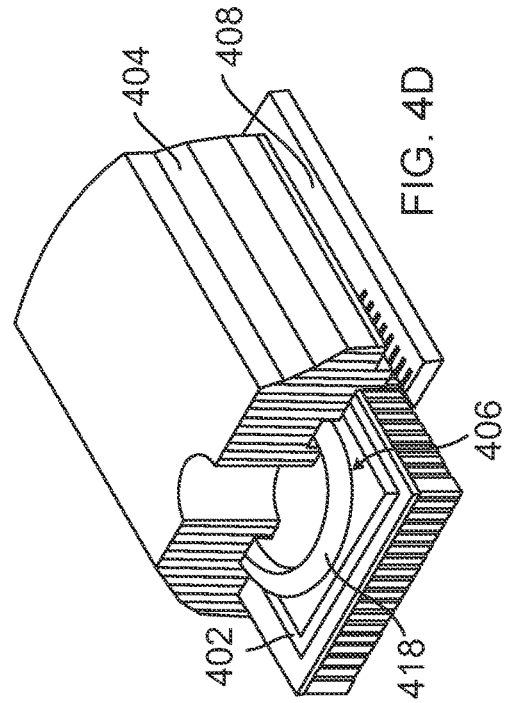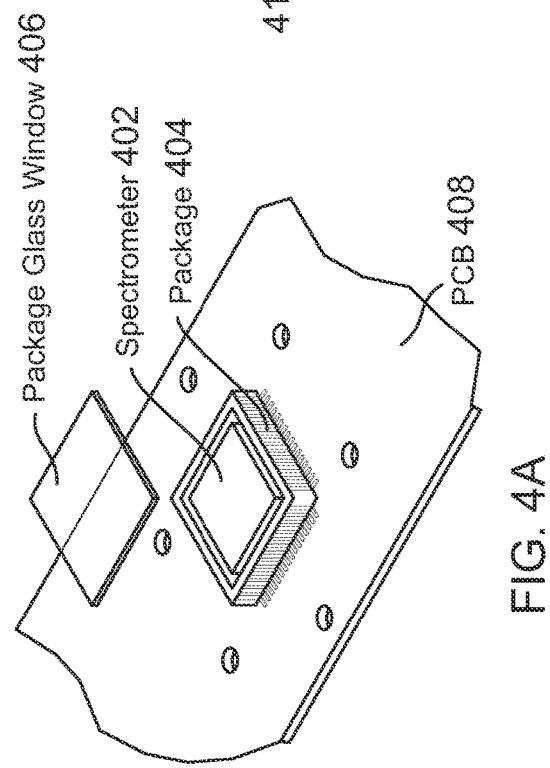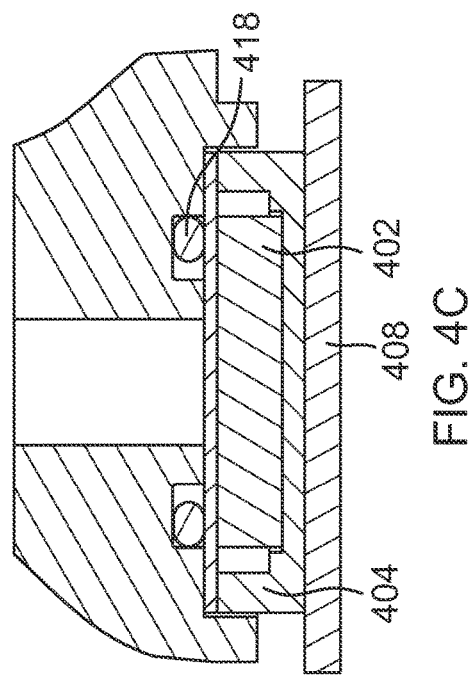

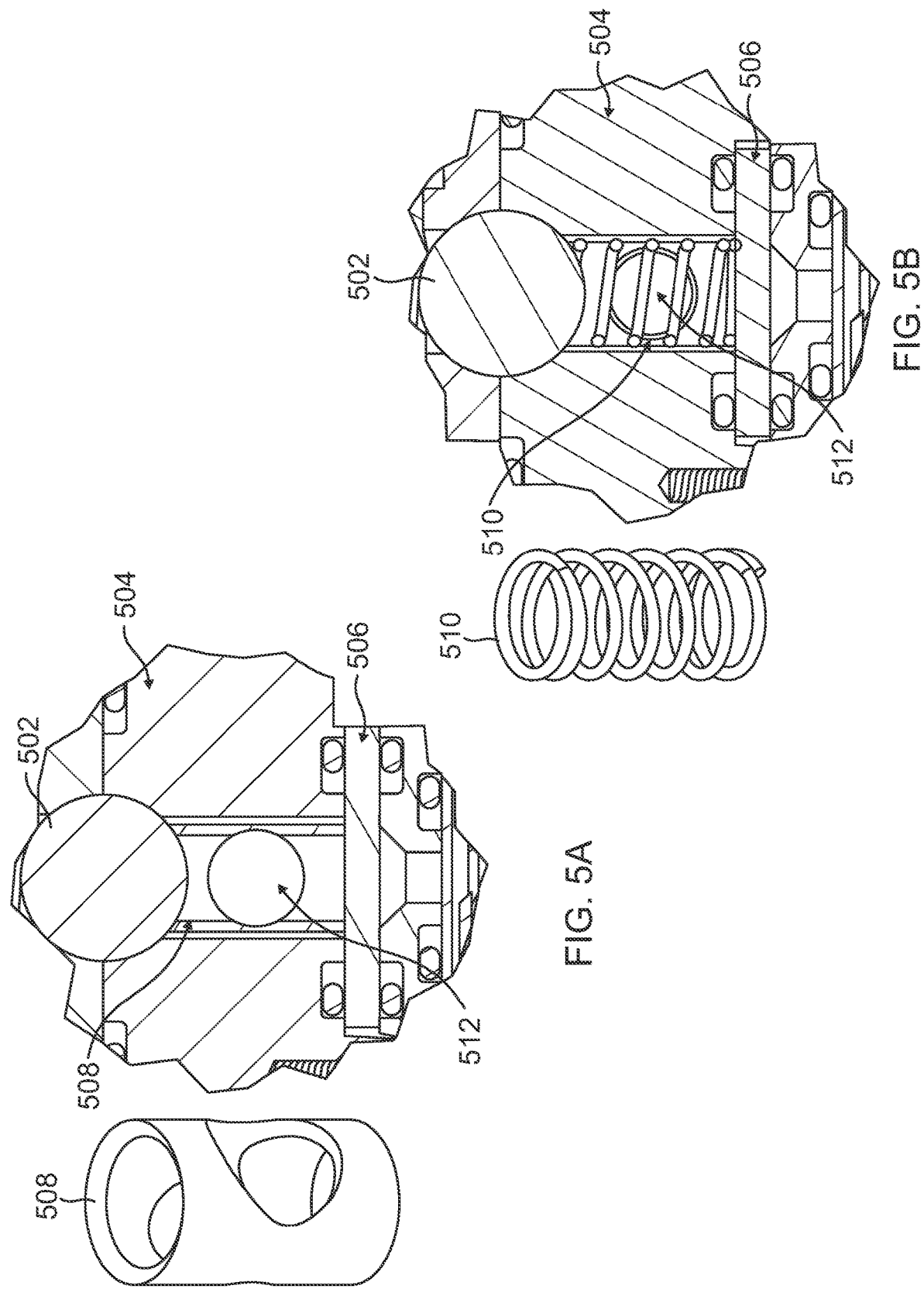

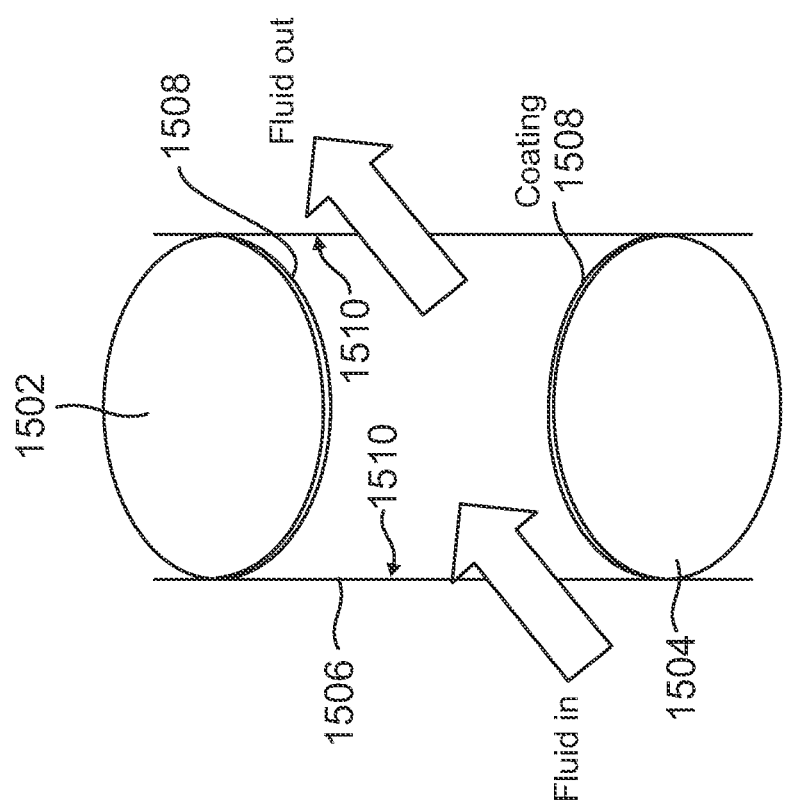

OPTICAL FLUID ANALYZER

PRIORITY CLAIM

This application claims priority to and the benefit of Provisional Application No. 63/210,450, filed in the U.S. Patent and Trademark Office on Jun. 14, 2021, the entire content of which is incorporated herein by reference as if fully set forth below in its entirety and for all applicable purposes.

TECHNICAL FIELD

The technology discussed below relates generally to optical spectroscopy, and in particular, to mechanisms to a spectroscopic optical fluid analyzer.

BACKGROUND

A fluid cell may be filled with a fluid, such as a liquid, gas, or plasma. The fluid inside the gas cell may be detected by sending light through the fluid cell. A portion of the light is absorbed by the fluid, while the rest may be detected, for example, by a spectrometer. Miniaturization of fluid analyzers may be achieved using a micro-electro-mechanical-systems (MEMS) spectrometer, such as a Fourier Transform Infrared (FTIR) spectrometer. In addition, miniaturization of fluid analyzers may allow for integration of fluid analyzers with sensors and other components and enable mass production of integrated devices for fluid analysis.

SUMMARY

The following presents a summary of one or more aspects of the present disclosure, in order to provide a basic understanding of such aspects. This summary is not an extensive overview of all contemplated features of the disclosure and is intended neither to identify key or critical elements of all aspects of the disclosure nor to delineate the scope of any or all aspects of the disclosure. Its sole purpose is to present some concepts of one or more aspects of the disclosure in a form as a prelude to the more detailed description that is presented later.

Various aspects of the disclosure relate to an optical fluid analyzer including a fluid cell configured to receive a sample (e.g., a fluid, such as a liquid, gas, or plasma) under test. Input light is sent through the fluid cell, where a portion of the light is absorbed by the fluid and the remaining portion of the light can be detected by a spectrometer. In some examples, the spectrometer may be implemented as a micro-electro-mechanical-systems (MEMS) spectrometer. Optical elements are used to seal the fluid cell on opposing sides thereof and to allow the light to enter and exit the fluid cell. In addition, the optical elements allow the light spectrum to be transmitted therethrough with a negligible absorption value.

The optical fluid analyzer further includes a machine learning (ML) engine, such as an artificial intelligence (AI) engine, that is configured to generate a result defining at least one parameter of the fluid based on a spectrum produced by the spectrometer. For example, the AI engine may be configured to predict the measured fluid and its concentration. Other parameters, such as the energy content in the fluid, the total volatile organic compound, the amount of particulate matter in the fluid, and other suitable parameters may be estimated by the AI engine. In some examples, the AI engine may use correction and prediction models, such as chemometrics, Kalman filtering, etc., to predict or estimate the parameter(s).

In some examples, the optical fluid analyzer may be implemented as a spectroscopic lab-in-a-box for biological sample detection, such as for virus infection detection. The optical fluid analyzer may be suitable, for example, for mass screening in pandemic situations enabling ultra-rapid and low-cost analysis for non-specialized users. The optical fluid analyzer can further be scalable and be produced with large quantities. The fluid cell in the optical fluid analyzer is designed and implemented such that the fluid sealing is maintained for infection control purpose.

In an example, an optical fluid analyzer is disclosed. The optical fluid analyzer includes a light source configured to generate input light, a fluid cell configured to receive a fluid, a first optical window configured to seal the fluid cell on a first side thereof and a second optical element configured to seal the fluid cell on a second side thereof. The first optical element is further configured to direct the input light into the fluid cell on the first side thereof, and the second optical element is further configured to receive output light from the fluid cell via the second side thereof. The optical fluid analyzer further includes a spectrometer configured to receive the output light via the second optical element and to obtain a spectrum of the fluid based on the output light, and a machine learning engine configured to receive the spectrum and to generate a result defining at least one parameter of the fluid.

These and other aspects of the invention will become more fully understood upon a review of the detailed description, which follows. Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

BRIEF DESCRIPTION OF THE DRAWINGS

FIGS. 3A and 3B are diagrams illustrating an optical fluid analyzer including a ball seat sealing system according to some aspects.

FIGS. 4A-4D are diagrams illustrating an example of an optical fluid analyzer including a package glass window sealing system according to some aspects.

FIGS. 5A and 5B are diagrams illustrating examples of ball lens configurations according to some aspects.

FIG. 15 is a diagram illustrating an example of a fluid cell design according to some aspects.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Figure 1:
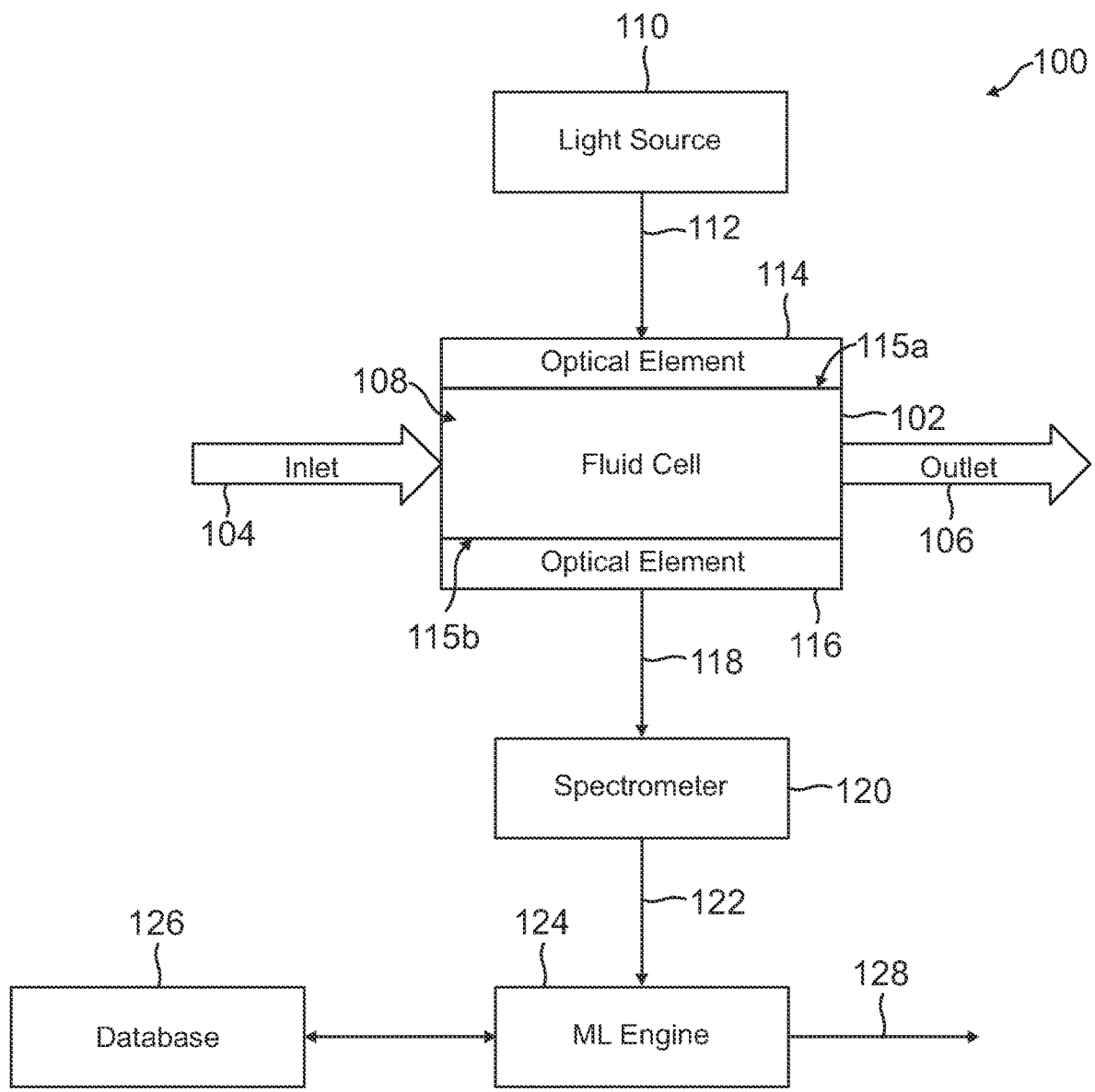
FIG. 1 is a diagram illustrating an optical fluid analyzer according to some aspects.

FIG. 1 is a diagram illustrating an optical fluid analyzer 100 according to some aspects. In some examples, the optical fluid analyzer 100 may be a portable, handheld device. The optical fluid analyzer 100 includes a fluid cell 102. A fluid 108 (e.g., a gas, liquid, or plasma) may enter the fluid cell 102 via one or more fluid inlets 104. In addition, the fluid 108 may exit the fluid cell 102 via one or more fluid outlets 106. The fluid 108 inside the fluid cell 102 may be detected by directing input light 112 from a light source 110 into the fluid cell 102 via a first optical element 114. The first optical element 114 may be configured to seal the fluid cell 102 on a first side 115a thereof and to direct the input light 112 into the fluid cell 102 on the first side 115a thereof.

A portion of the input light 112 may be absorbed by the fluid, while the remainder of the light may be output from the fluid cell 102 as output light 118 via a second optical element 116. The second optical element 116 may be configured to seal the fluid cell 102 on a second side 115b thereof and to direct the output light 118 from the fluid cell 102 to a spectrometer 120. In some examples, the first and second optical elements 114 and 116 may be flat optical windows, such as sapphire windows. In other examples, the first optical element 114 and/or the second optical element 116 may include one or more optical coupling elements, such as ball lenses, half-ball lenses, or Plano convex lenses. In some examples, the optical fluid analyzer 100 may include optical coupling elements in addition to the optical elements 114 and 116. For example, the optical fluid analyzer 100 may include one or more reflectors (e.g., mirrors), lenses, or other suitable optical coupling elements.

In some examples, the fluid cell 102 has an optimum cell length that balances light absorption by the fluid 108 and saturation of the absorption signal. For example, increasing the fluid cell length may increase light absorption by the fluid 108. As light absorption increases, low fluid concentrations are easier to detect. However, if the fluid cell length is too long, the absorption signal may saturate for fluids 108 having relatively high concentrations.

The spectrometer 120 may be, for example, a Fourier Transform infrared (FTIR) spectrometer configured to produce an interferogram that may be detected by a detector (e.g., an InGaAs photo detector) of the spectrometer 120. The output of the detector may then be processed by the spectrometer 120 to obtain a spectrum 122 of the detected light. In some examples, the spectrometer 120 may include a Michelson interferometer or a Fabry-Perot interferometer.

In some examples, the spectrometer 120 may be implemented, for example, as a micro-electro-mechanical-systems (MEMS) spectrometer, such as a MEMS FTIR spectrometer. As used herein, the term MEMS refers to the integration of mechanical elements, sensors, actuators and electronics on a common substrate through microfabrication technology. For example, the microelectronics are typically fabricated using an integrated circuit (IC) process, while the micromechanical components are fabricated using compatible micromachining processes that selectively etch away parts of the silicon wafer or add new structural layers to form the mechanical and electromechanical components. One example of a MEMS element is a micro-optical component having a dielectric or metallized surface working in a reflection or refraction mode. Other examples of MEMS elements include actuators, detector grooves, and fiber grooves. In some examples, a MEMS spectrometer may include one or more micro-optical components (e.g., one or more reflectors or mirrors) that may be moveably controlled by a MEMS actuator. For example, the MEMS spectrometer may be fabricated using a deep reactive ion etching (DRIE) process on a silicon-on-insulator (SOI) substrate in order to produce the micro-optical components and other MEMS elements that are able to process free-space optical beams propagating parallel to the SOI substrate.

The spectrum 122 may be input to a machine learning (ML) engine 124, such as an AI engine, to generate a result 128 defining at least one parameter of the fluid 108. For example, the result 128 may identify the fluid or obtain other parameters associated with the fluid, such as the concentration of the fluid, the energy content in the fluid, the total volatile organic compound, the amount of particulate matter in the fluid, the microparticles suspended in the fluid, or other suitable parameters. In some examples, the ML engine 124 may use correction and prediction models, such as chemometrics, Kalman filtering, etc., to predict or estimate the parameter(s). In some examples, the ML engine 124 may access an optional database 126 containing fluid data to generate the result 128. For example, the fluid data stored on the database 126 may be utilized to train the ML engine 124.

In an example, the fluid data may contain spectrum parameters for known fluids and fluid concentrations. In some examples, the optical fluid analyzer 100 may include a memory on which the database 126 is stored.

Figure 2:
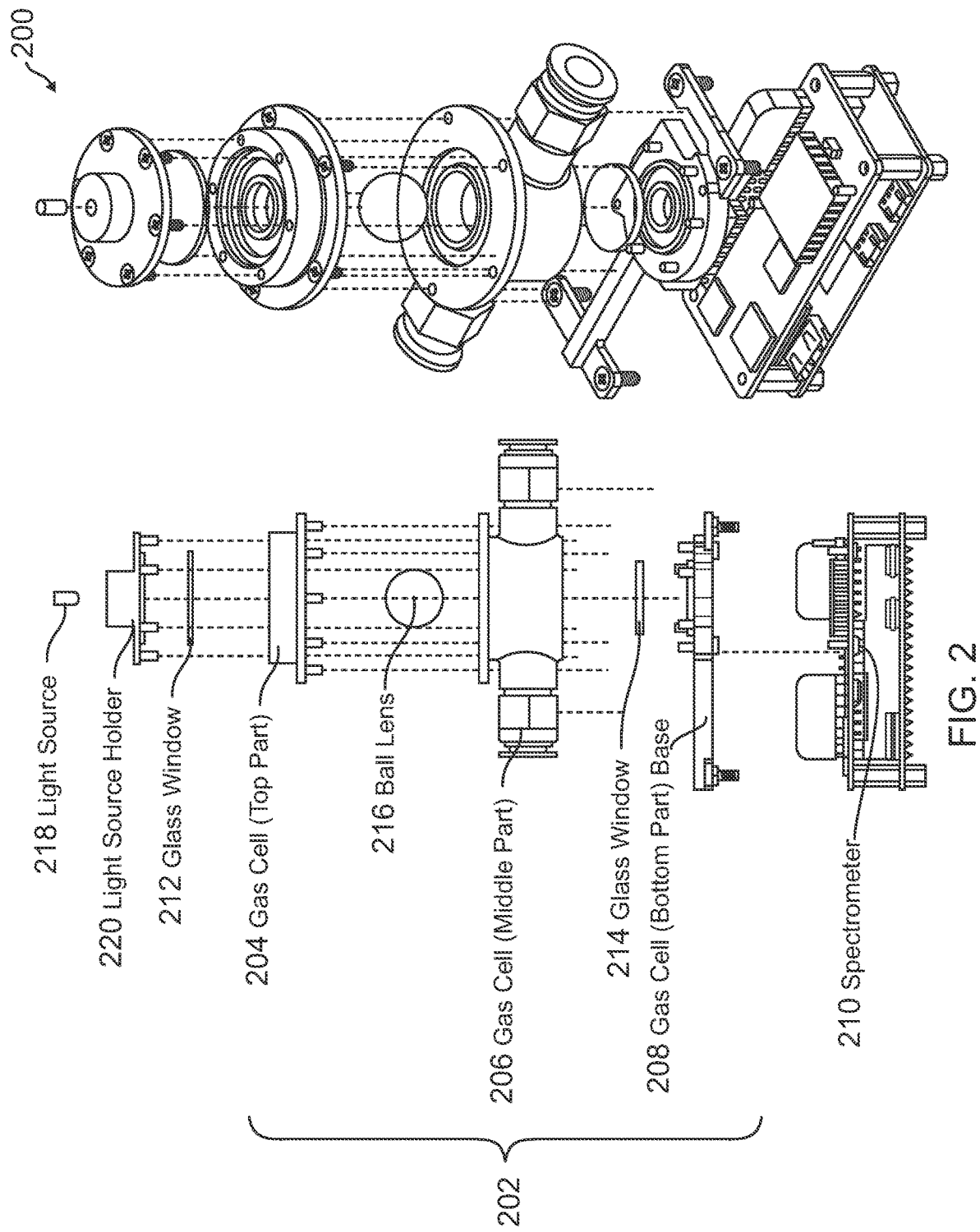
FIG. 2 is a diagram illustrating exploded views of an example of an optical fluid analyzer according to some aspects.

FIG. 2 is a diagram illustrating exploded views of an example of an optical fluid analyzer 200 according to some aspects. The optical fluid analyzer 200 includes a fluid cell 202 (gas cell), a spectrometer 210, a light source 218, and a light source holder 220 configured to hold the light source 218 in place. The gas cell 202 includes three main parts: a top part 204, a middle part 206, and a bottom part 208. The top part 204 is responsible for preserving the optical alignment between the light source 218 and the fluid cell 202 and includes an opening configured to receive a first optical window (glass window) 212. The middle part 206 is the main part of the fluid cell 202 that is configured to receive a fluid. For example, the middle part 206 may be coupled to a fluid inlet to receive a fluid and a fluid outlet to pass the fluid out of the fluid cell 202. For the fluid cell I/O (between the fluid inlet/outlet and the fluid cell), sealed quick connectors may be used to seal the flow of the fluids and to ease the installation of the air tubing. The middle part 206 may further be coupled to one or more optical coupling elements 216 configured to direct input light from the light source 218 into the fluid cell. In the example shown in FIG. 2, the optical coupling element(s) include a ball lens 216 coupled between the first optical window 212 and the fluid cell 202.

The bottom part 208 of the fluid cell 202 is responsible for preserving the optical alignments between the spectrometer 210 and the rest of the parts. The bottom part 208 includes walls surrounding the spectrometer 210 to provide a physical alignment of the spectrometer 210 with the remaining parts of the fluid cell 202. The bottom part 208 further includes an opening configured to receive a second optical window (glass window) 214. The first and second optical windows 212 and 214 are further configured to seal the fluid cell 202 from the top and bottom sides. In some examples, the first and second optical windows 212 and 214 may be flat optical windows, such as sapphire glass windows. The flat optical windows 212 and 214 are configured to allow the infrared spectrum to be transmitted with a very small absorption value. In some examples, the fluid cell parts 204, 206, and 208 may be nickel-plated to prevent corrosion due to some fluids.

When using a ball lens in a sealed optical setup, as shown in FIG. 2, the ball lens 216 is inserted between the two flat optical windows 212 and 214. The two flat optical windows 212 and 214 can seal the fluid cell 202 with the use of O-rings (not specifically shown in FIG. 2). According to O-ring design guides, O-rings cannot be used directly with the ball lens 216 in examples in which the ball lens 216 is in contact with a flat surface (e.g., flat optical windows 212 and 214) to maintain a homogeneous pressure over the surface contact area. Therefore, in some examples, ball seats may be used in lieu of O-rings to seal the fluid cell 202. Ball seats may replace not only the O-rings, but the entire sealing system including the flat optical window 212.

FIGS. 3A and 3B are diagrams illustrating an optical fluid analyzer 300 including a ball seat sealing system according to some aspects. The optical fluid analyzer 300 includes a ball lens 302 surrounded by ball seats 304 and 306. The inner surface curvature of the ball seats 304 and 306 is configured to match the lens surface curvature of the ball lens 302 to increase surface contact, thereby increasing the sealing efficiency. In some examples, the ball seats 304 and 306 may be formed of rubber.

The optical fluid analyzer 300 further includes a fluid cell (gas cell) 308, an optical window 310, a spectrometer 312, a fluid inlet 316, a fluid outlet 318, and a light source 320. An O-ring 314 is configured to seal the spectrometer 312. The fluid inlet 316 and fluid outlet 318 are configured to allow a fluid (e.g., liquid, gas, or plasma) to enter and exit the fluid cell 308. The ball lens 302 and ball lens seats 304 and 306 form an optical element configured to seal the fluid cell 308 on a first side thereof. In addition, the ball lens 302 is further configured to direct input light from the light source 320 into the fluid cell 308. The optical window 310 is configured to seal the fluid cell 308 on a second side thereof opposite the first side and to direct output light from the fluid cell into the spectrometer 312. The fluid cell 308 and spectrometer 312 may be assembled on a substrate 322 (e.g., a printed circuit board (PCB)). In some examples, a ML engine and associated database (e.g., memory), not shown for simplicity, may further be assembled on the substrate 322. Various sensors, such as pressure sensors, temperature sensors, fluid flow sensors, and other suitable sensors may further be integrated on the substrate 322.

In the example shown in FIG. 3B, the fluid cell 308 is a separate unit from the spectrometer 312, such that each of the systems (optical, electrical, and mechanical) are separated from one another. This can lead to an increase in the overall size and in the number of components used. In addition, by separating the spectrometer 312 and the fluid cell 308 without any sealing between them, parasitic fluids can infiltrate the optical path, leading to incorrect reading. Therefore, in some examples, a package glass window may replace the fluid cell optical window 310 to be directly in contact with both the fluid and the spectrometer package.

FIGS. 4A-4D are diagrams illustrating an example of an optical fluid analyzer 400 including a package glass window sealing system according to some aspects. The optical fluid analyzer 400 includes a spectrometer 402 integrated within a package 404 that is assembled on a substrate 408 (e.g., a PCB). The package 404 includes an opening configured to receive a package glass window 406.

The optical fluid analyzer 400 further includes a ball lens 410, ball lens seats 412 and 414 surrounding the ball lens 410, and a fluid cell 416. The ball lens 410 and ball lens seats 412 and 414 form an optical element configured to seal the fluid cell 416 on a first side thereof. In addition, the ball lens 410 is further configured to direct input light from a light source (not shown) into the fluid cell 416. The package glass window 404 is configured to seal the fluid cell 416 on a second side thereof opposite the first side and to direct output light from the fluid cell 416 into the spectrometer 402. In particular, the package glass window 404 is configured to provide sealing directly between the fluid cell 416 and the spectrometer 402. An O-ring 418 may be used to maintain the sealing between the package glass window 404 and the fluid cell 416, thereby preventing parasitic leakage of the fluid.

In examples in which a ball lens is used as an optical coupling element to couple the input light into the fluid cell (e.g., as shown in any of FIG. 2, 3A, 3B, or 4B), a slight dislocation of the lens can cause discrepancies in the optical signal and overall spectrum measured. For example, if a housing containing the ball lens is fabricated with a tight clearance between the ball lens and the housing, any variation may prevent the top part of the housing from being assembled with the lower part of the housing. This in turn may lead to a fluid leakage. Therefore, in some examples, a rubber spacer or spring may be added to fix the position of the ball lens.

FIGS. 5A and 5B are diagrams illustrating examples of ball lens configurations according to some aspects. In FIGS. 5A and 5B, a ball lens 502 is positioned in a housing 504 and configured to seal a fluid cell 512 on a first side thereof. An optical window 506 (e.g., a flat sapphire window) is further configured to seal the fluid cell 512 on a second side thereof opposite the first side. In FIG. 5A, a rubber spacer 508 is shown coupled between the ball lens 502 and the flat optical window 506. In FIG. 5B, a spring 510 is shown coupled between the ball lens 502 and the flat optical window 506. Neither the rubber spacer 508 nor the spring 510 block the fluid flow through the fluid cell 512. In addition, each of the rubber spacer 508 and the spring 510 produce a pressure on the ball lens 502, which in turn, fixes the ball lens 502 in position, thus preventing any change in its position due to motions or vibrations of the housing 504.

In the examples shown in FIGS. 3A-5B, the optical coupling element may include a light source and a ball lens that focuses the light into the MEMS spectrometer. This design provides simplicity since a balls lens is the only optical component and the ball lens is used in sealing. This design may be used, for example, for gases where there is no difference between the gases refractive index and air, so the flow of gases may not affect the focusing and optical coupling of the design. However, measuring liquids or other fluids that have significant variation in the refractive index may affect the optical coupling. Therefore, in some examples, the optical coupling may be performed by a collimated design in which the fluid type may not affect the optical coupling.

Figure 6B:
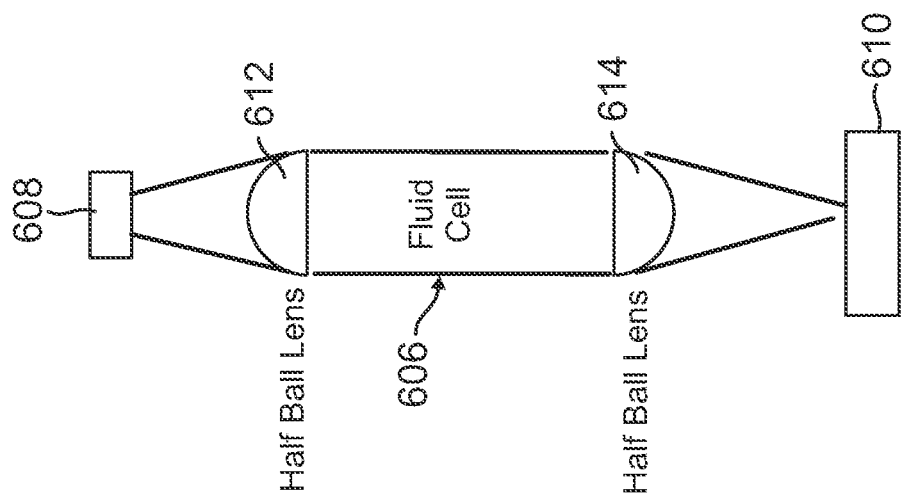
FIGS. 6A and 6B are diagrams illustrating examples of collimated optical coupling designs according to some aspects.
Figure 6A:
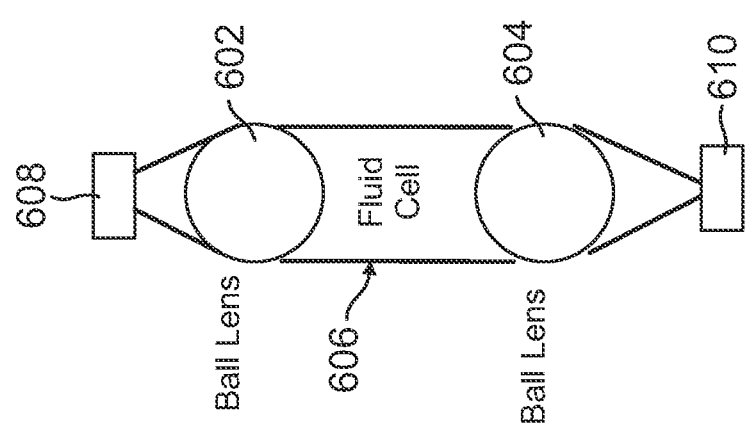

FIGS. 6A and 6B are diagrams illustrating examples of collimated optical coupling designs according to some aspects. In the example shown in FIGS. 6A and 6B, the optical coupling is performed using a collimated setup in which the fluid sample type does not impact the optical coupling. FIG. 6A illustrates a collimated optical coupling design using two ball lenses 602 and 604, whereas FIG. 6B illustrates a collimated optical coupling design using two half-ball lenses 612 and 614. In each design, the two ball lenses 602 and 604 or two half-ball lenses 612 and 614 couple input light from a light source 608 into a fluid cell 610 on a first side thereof and receive and couple output light from the fluid cell via a second side thereof into a spectrometer 610. The ball lenses 602 and 604 or half-ball lenses 612 and 614 may provide not only optical coupling, but also sealing of the fluid cell 610 (e.g., using ball lens seats or O-rings, as described above). The two ball lenses 602 and 604 design in FIG. 6A is less sensitive and more compact in terms of distance between the infrared source 608 and the lenses 602 and 604, while the two half-ball lenses 612 and 614 design is easier in term of sealing the fluid cell 610 (e.g., O-rings may be used for sealing instead of ball lens seats).

Figure 7:
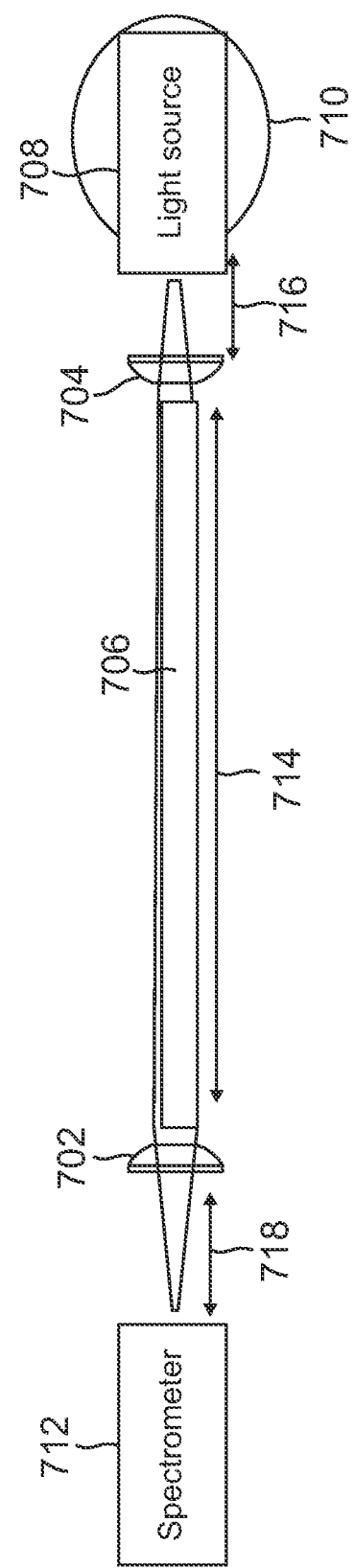
FIG. 7 is a diagram illustrating another example of a collimated optical coupling design according to some aspects.

FIG. 7 is a diagram illustrating another example of a collimated optical coupling design according to some aspects. In the example shown in FIG. 7, the ball or half-ball lenses can be replaced by Plano convex lenses 702 and 704. In addition, the collimated setup uses a reflector 710 inserted behind the light source 708 to collect back rays of the light source and reflect the back rays towards the Plano convex lens 704 for coupling into a fluid cell 706 to nearly double the optical power. In some examples, the Plano convex lenses 702 and 704 may be calcium fluoride lenses with focal lengths 716 and 718 of 18 mm to accommodate a fluid path length 714 of 50 mm. It should be understood that the focal lengths 716 and 718 and fluid path length 714 are variable and not limited to the examples provided herein. In some examples, the Plano convex lenses 702 and 704 may provide sealing of the fluid cell 706. In other examples, additional flat optical windows may be used for sealing the fluid cell 706.

Figure 8:
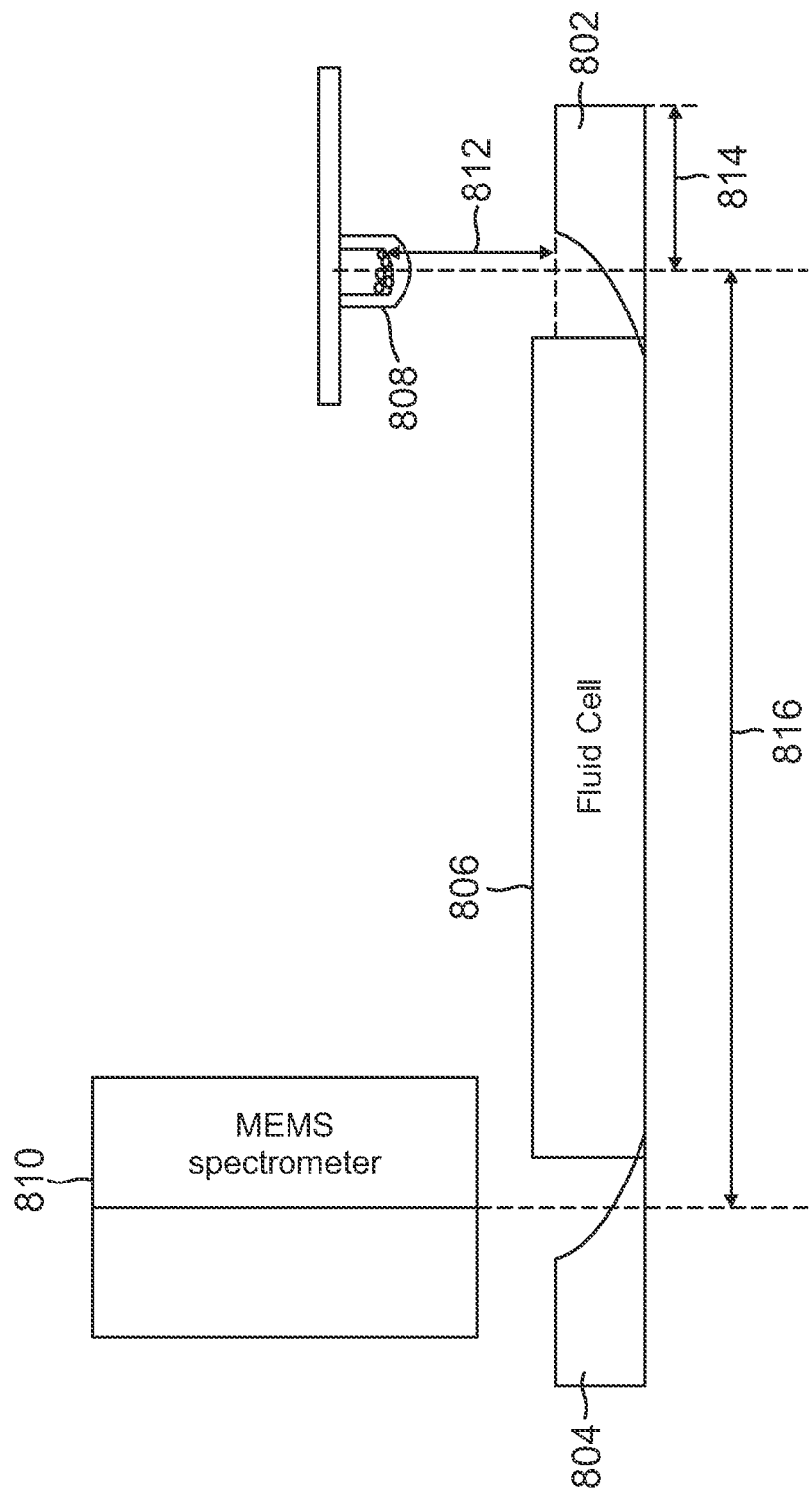
FIG. 8 is a diagram illustrating another example of a collimated optical coupling design according to some aspects.

FIG. 8 is a diagram illustrating another example of a collimated optical coupling design according to some aspects. In the example shown in FIG. 8, the collimating design includes two off-axis parabolic mirrors 802 and 804. The off-axis parabolic mirror 802 is configured to receive input light from a light source 808 and reflect (redirect) the input light into a fluid cell 806 on a first side thereof. In addition, the off-axis parabolic mirror 804 is configured to receive output light from the fluid cell 806 on a second side thereof and to reflect (redirect) the output light into a spectrometer 810. The fluid cell 806 may be sealed using flat optical windows (not shown), as described above.

The off-axis parabolic mirrors 802 and 804 provide a wide spectrum range of metallic reflection and avoid the Fresnel optical loss of the lens designs shown in FIGS. 6A, 6B, and 7. In addition, the mirrors 802 and 804 may be manufactured by plastic molding that allows high volume with low cost. In some examples, a single plastic mold including both mirrors 802 and 804 may be used to accommodate any sensitivity of the alignment in the design shown in FIG. 8.

In some examples, the off-axis parabolic mirror 802 has a focal length of 15 mm, and the off-axis parabolic mirror 804 has a focal length of 25 mm. In this example, a distance 812 between the light source 808 and the off-axis parabolic mirror 802 may be 8.65 mm and the off-axis parabolic mirrors 802 and 804 may each have a width 814 of 12.3 mm with a fluid cell length 816 of 100 mm. It should be understood that the focal lengths, distance 812, width 814 of the mirrors 802 and 804, and fluid cell length 816 are variable, and not limited to the examples provided herein.

Figure 9:
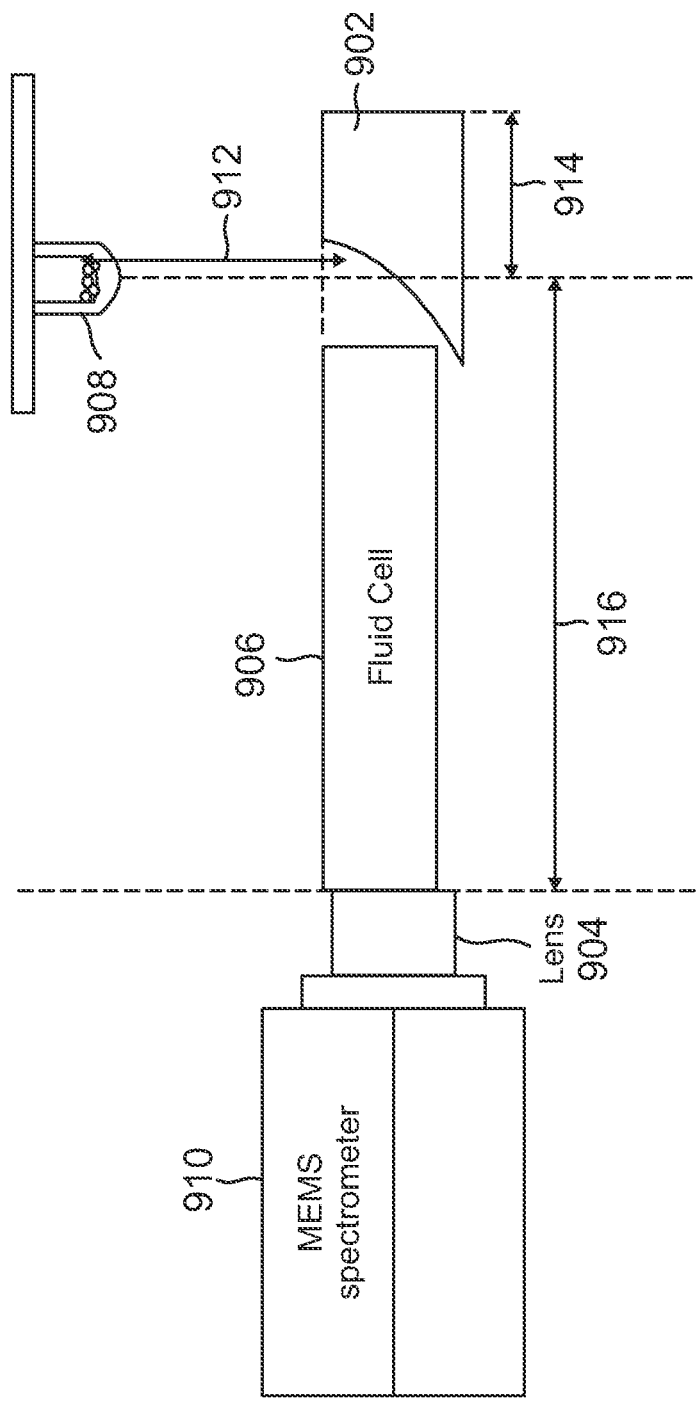
FIG. 9 is a diagram illustrating another example of a collimated optical coupling design according to some aspects.

FIG. 9 is a diagram illustrating another example of a collimated optical coupling design according to some aspects. In the example shown in FIG. 9, the collimating design includes an off-axis parabolic mirror 902 and a lens 904. The off-axis parabolic mirror 902 is configured to receive input light from a light source 908 and reflect (redirect) the input light into a fluid cell 906 on a first side thereof. In addition, the lens 904 is configured to receive output light from the fluid cell 906 on a second side thereof and to reflect (redirect) the output light into a spectrometer 910. In some examples, the lens 904 may be a calcium fluoride lens. The fluid cell 906 may be sealed using flat optical windows (not shown) or using a combination of a flat optical window adjacent to the off-axis parabolic mirror 902 and the lens 904. In some examples, the lens 904 may be coated to facilitate calibration of the optical fluid analyzer.

In some examples, the off-axis parabolic mirror 902 has a focal length of 15 mm and the lens 904 has a focal length of 18 mm. In this example, a distance 912 between the light source 908 and the off-axis parabolic mirror 902 may be 8.65 mm and the off-axis parabolic mirror 902 may have a width 914 of 12.3 mm with a fluid cell length 916 of 100 mm. It should be understood that the focal lengths, distance 912, width 914 of the mirrors 902 and 904, and fluid cell length 916 are variable, and not limited to the examples provided herein.

Figure 10B:
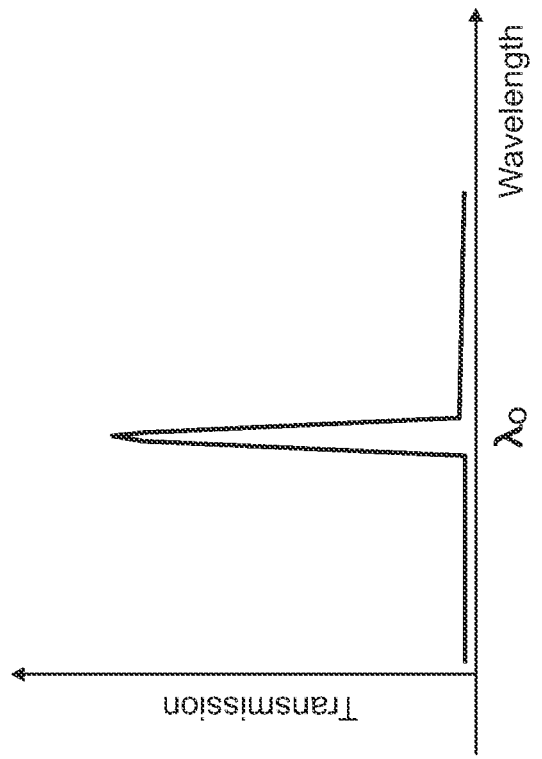
FIGS. 10A and 10B are diagrams illustrating an example optical coupling design for calibration of the optical fluid analyzer according to some aspects.
Figure 10A:
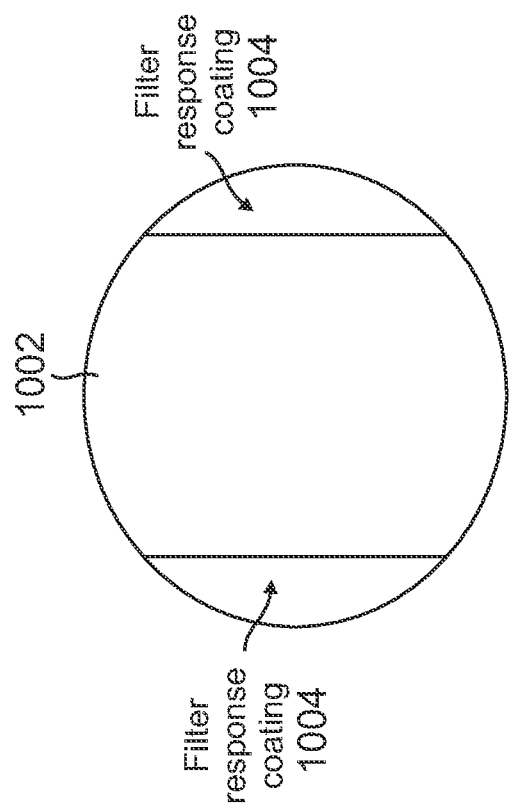

FIGS. 10A and 10B are diagrams illustrating an example optical coupling design for calibration of the optical fluid analyzer according to some aspects. The optical coupling design shown in FIG. 10 includes a ball lens 1002 having a filter response coating 1004 on opposing ends thereof. The center area of the ball lens 1002 is not coated with the filter response coating 1004. The coating 1004 absorbs all wavelengths except for a reference wavelength $\lambda_o$ used by the calibration. The response of the coating 1004 is shown in FIG. 10B.

Figure 11B:
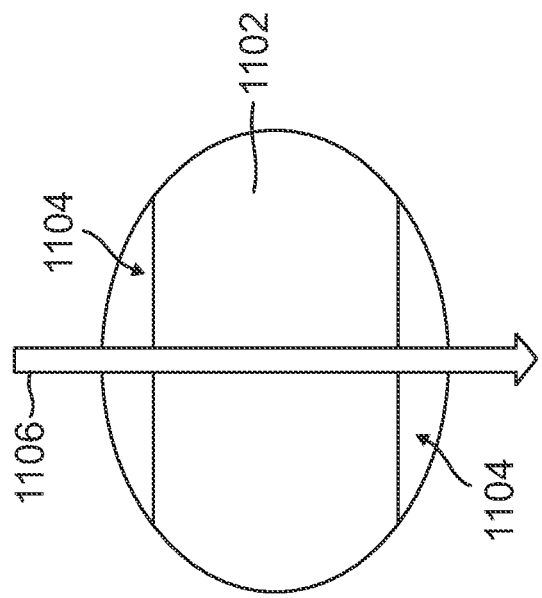
FIGS. 11A and 11B illustrate exemplary modes of operation of a coated ball lens according to some aspects.
Figure 11A:
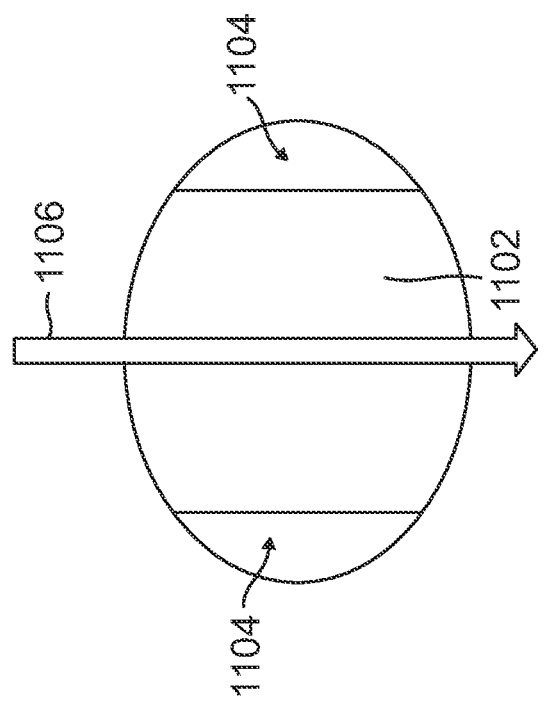

FIGS. 11A and 11B illustrate exemplary modes of operation of a coated ball lens 1102 according to some aspects. In a first mode, as shown in FIG. 11A, the filter response coating 1104 of the ball lens 1102 is out of a light path 1106 of input light from a light source (not shown). Therefore, no absorption of the input light occurs and the spectrum reflects the absorption of the fluid in a fluid cell (not shown). In a second mode, as shown in FIG. 11B, the light path 1106 of the input light passes through the filter response coating 1104 of the ball lens 1102, and as a result, absorption occurs producing the spectrum shown in FIG. 10B. The second mode may thus be referred to as a calibration mode. For example, in the calibration mode, the value of the wavelength $\lambda_o$ may be compared to a reference design value using, for example, digital signal processing. Calibration and drift correction may then be performed based on the comparison. For example, the optical fluid analyzer may be configured to calibrate the machine learning engine during the calibration mode.

Figure 12:
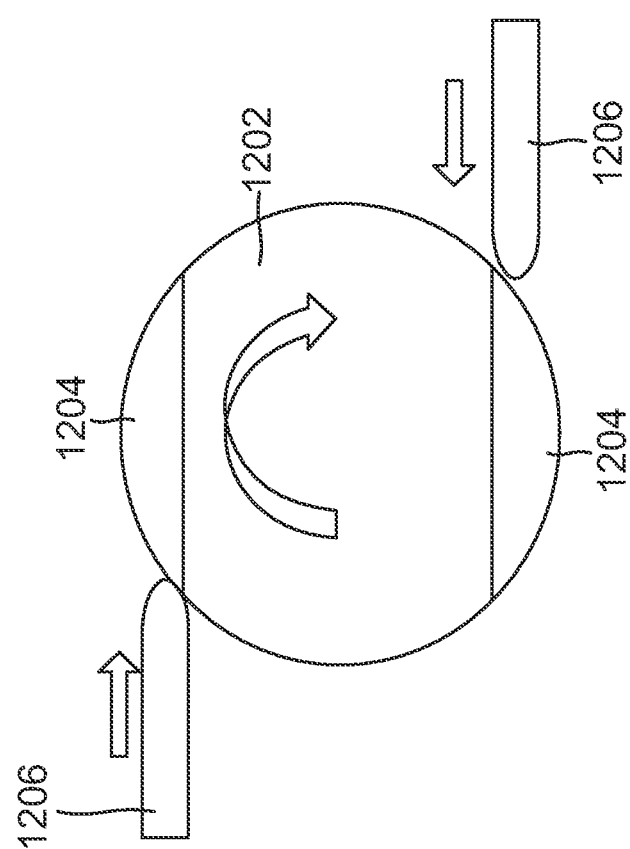
FIG. 12 is a diagram illustrating an exemplary mode-switching operation according to some aspects.

FIG. 12 is a diagram illustrating an exemplary mode-switching operation according to some aspects. In the example shown in FIG. 12, a ball lens 1202 includes a filter response coating 1204 on opposing ends thereof, as in FIGS. 10A, 11A, and 11B. A rotation device 1206 is coupled to the ball lens 1202 and configured to rotate the ball lens 1202 between a first orientation (e.g., the first mode shown in FIG. 11A) in which the input light passes through the ball lens 1202 without passing through the filter response coating 1204 and a second orientation (e.g., the second mode shown in FIG. 11B) in which the input light passes through the filter response coating 1204 of the ball lens 1202. For example, the rotation device 1206 may include springs and fingers that are controlled by the optical fluid analyzer to produce a 90 degree rotation of the ball lens 1202 between the two modes of operation.

Figure 13:
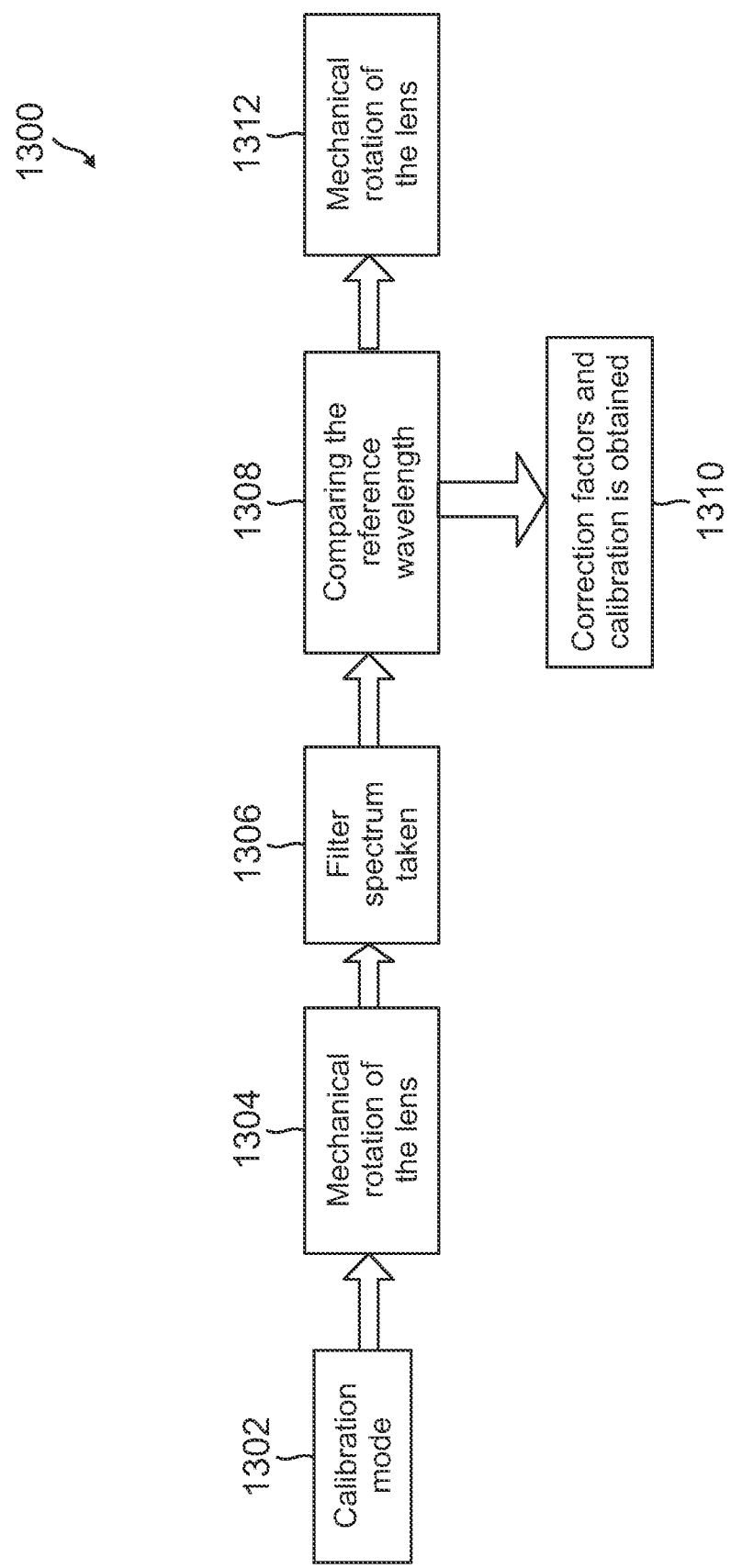
FIG. 13 is a flow chart illustrating an exemplary process for calibrating an optical fluid analyzer including a coated ball lens according to some aspects.

FIG. 13 is a flow chart illustrating an exemplary process for calibrating an optical fluid analyzer including a coated ball lens according to some aspects. At block 1302, the optical fluid analyzer may enter a calibration mode of the device. At block 1304, the optical fluid analyzer may mechanically rotate the coated ball lens (e.g., using the rotation device shown in FIG. 12) 90 degrees to the second orientation shown in FIG. 11B, such that the filter response coating of the ball lens is within the light path of the input light from the light source. At block 1306, the optical fluid analyzer may obtain a spectrum when the coated ball lens is in the second orientation. At block 1308, the optical fluid analyzer may compare the spectrum to a reference wavelength. At block 1310, the optical fluid analyzer may obtain correction factors and calibration parameters based on the comparison. The correction factors and calibration parameters may then be used to train the machine learning engine. At block 1312, the optical fluid analyzer may mechanically rotate the coated ball lens (e.g., using the rotation device shown in FIG. 12) 90 degrees to the first orientation shown in FIG. 11A, such that the filter response coating of the ball lens is outside the light path of the input light from the light source to enable the optical fluid analyzer to obtain a spectrum of the fluid sample under test.

Figure 14B:
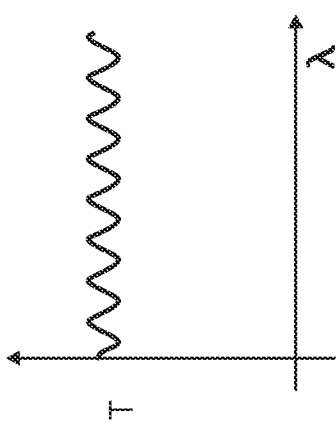
FIGS. 14A-14C are diagrams illustrating an optical coupling design with variable optical path length according to some aspects.
Figure 14C:
Figure 14A:
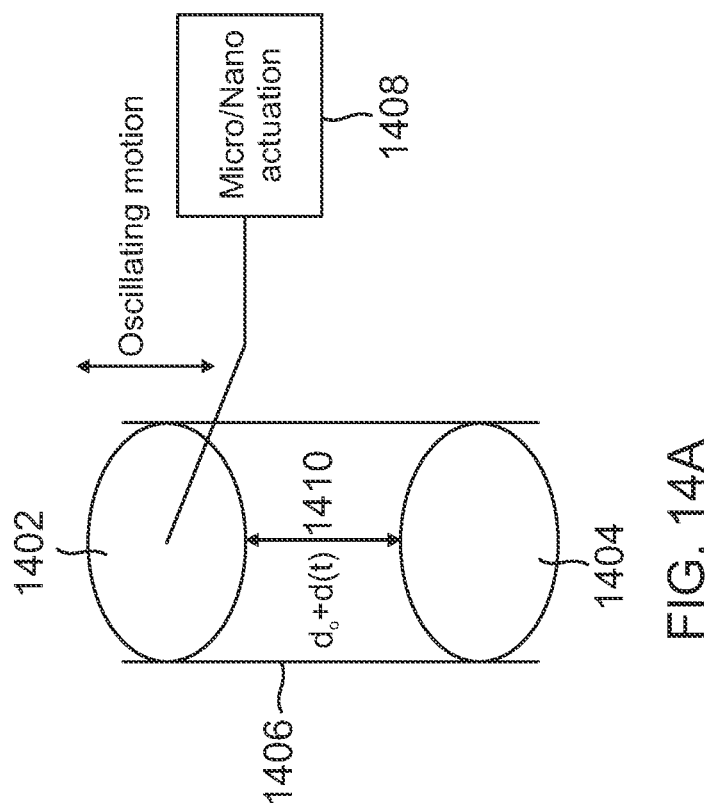

FIGS. 14A-14C are diagrams illustrating an example of an optical coupling design with variable optical path length according to some aspects. The optical coupling design includes two optical elements 1402 and 1404 for coupling input light into a fluid cell 1406 on a first side thereof and coupling output light from the fluid cell 1406 via a second side thereof. The optical elements 1402 and 1404 may include, for example, flat optical windows, ball lenses, half-ball lenses, Plano convex lenses, or other suitable optical coupling elements. To overcome the challenge of parasitic interference effect in a fluid cell 1406 due to the multiple reflections of light and the microscale path length 1410 in the fluid cell (e.g. 20 μm up to 100 μm), at least one of the optical elements (e.g., optical element 1402) can be coupled to an actuator 1408 (e.g., a micro/actuation mechanism) that is configured to cause motion of the optical element 1402 to continually vary the optical path length with motion d(t) in the fluid cell 1406 around a nominal value $d_o$, as shown in FIG. 14A. The continuous motion of the optical element 1402 results in dithering of the optical path length, such that the average value of d(t) is zero, as shown in by comparison between FIGS. 14B (with no oscillatory motion) and 14C (with oscillatory motion). In other examples, dithering of the optical path length may be achieved by electro-optic effect and/or thermo-optic effect applied on the optical element 1402. For example, an electric field may be applied across the optical element 1402 or a micro heater may be integrated with the optical element 1402.

FIG. 15 is a diagram illustrating an example of a fluid cell design according to some aspects. The fluid cell design includes two optical elements 1502 and 1504 configured to seal a fluid cell 1506 on either side thereof. To overcome the stiction of the fluid, for example, oil samples, within the fluid cell 1506, a coating 1508 can be applied on an internal surface (facing the fluid cell 1506) of at least one of the optical elements 1502 and 1504 to repel the fluid (e.g., prevent stiction of the fluid). In some examples, the coating 1508 can be hydrophobic or omni-phobic. As a result, the fluid may be purged easily without a need for a consumables cleaning solution. In some examples, the coating 1508 can be also applied on interior walls 1510 in the fluid cell 1506.

Figure 16:
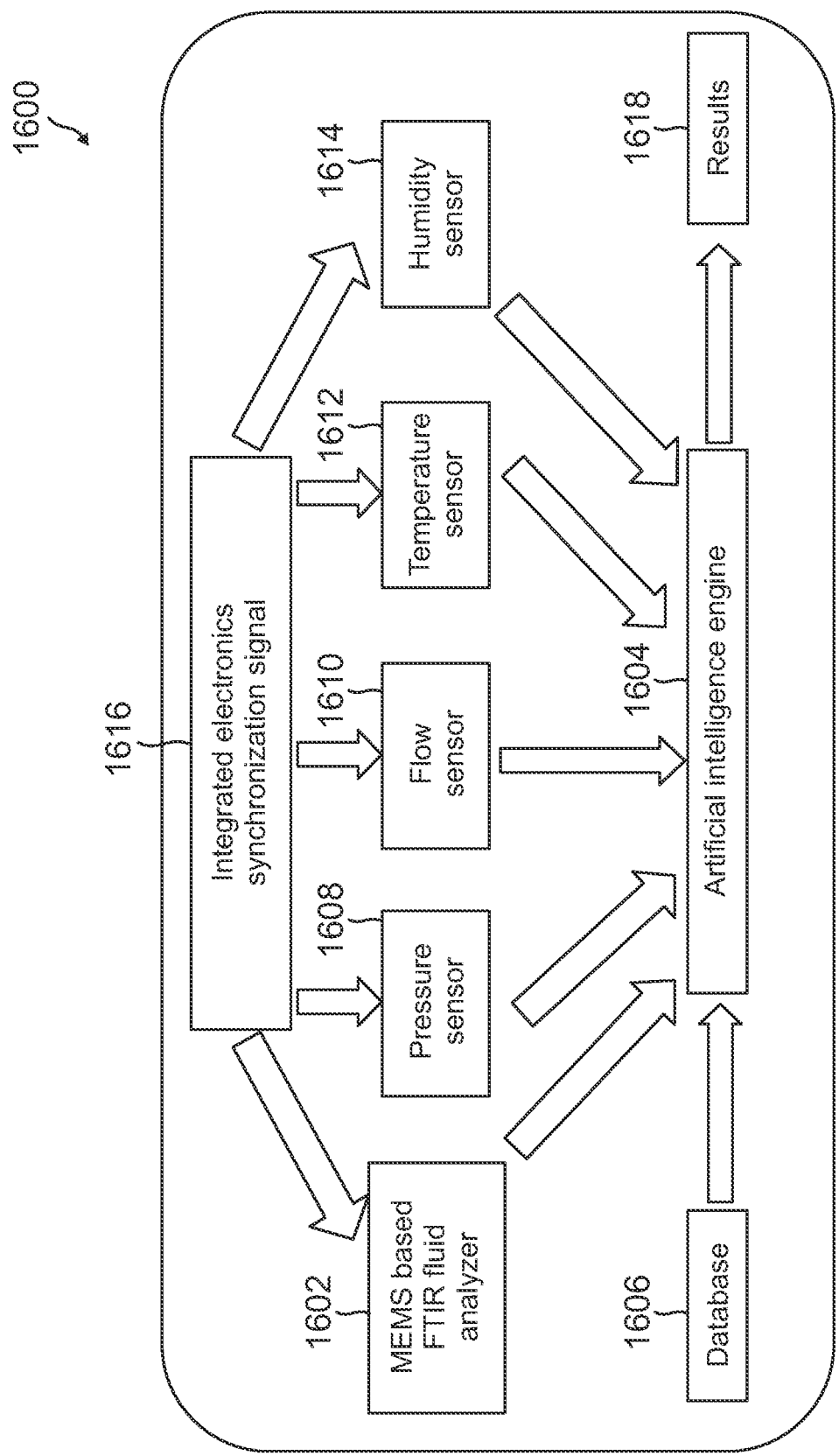
FIG. 16 is a diagram illustrating an example of an optical fluid analyzer integrated with other sensors according to some aspects.

FIG. 16 is a diagram illustrating an example of an optical fluid analyzer 1600 integrated with other sensors according to some aspects. The optical fluid analyzer 1600 includes a MEMS based FTIR fluid analyzer 1602 (e.g., including a light source, optical elements, fluid cell, and spectrometer (interferometer/detector)), artificial intelligence (AI) engine 1604 (e.g., ML engine), and database 1606 that are integrated with one or more other sensors. Examples of sensors include, but are not limited to, a pressure sensor 1608, a flow (fluid flow) sensor 1610, a temperature sensor 1612, and a humidity sensor 1614). The sensors 1608-1614 may be synchronized together and controlled via integrated electronics and synchronization signal circuitry 1616 to sense the fluid at the same time as the MEMS based FTIR fluid analyzer 1602 obtains a spectrum of the fluid. The output (e.g., sensor data related to the fluid in the fluid cell) of each sensor 1608-1614 may be input to the AI engine 1604, along with the spectrum of the fluid to aid the AI engine 1604 in predicting the fluid properties and specifications. The AI engine may further be trained with fluid data in the database 1606 to produce results 1618 related to the fluid.

Figure 17:
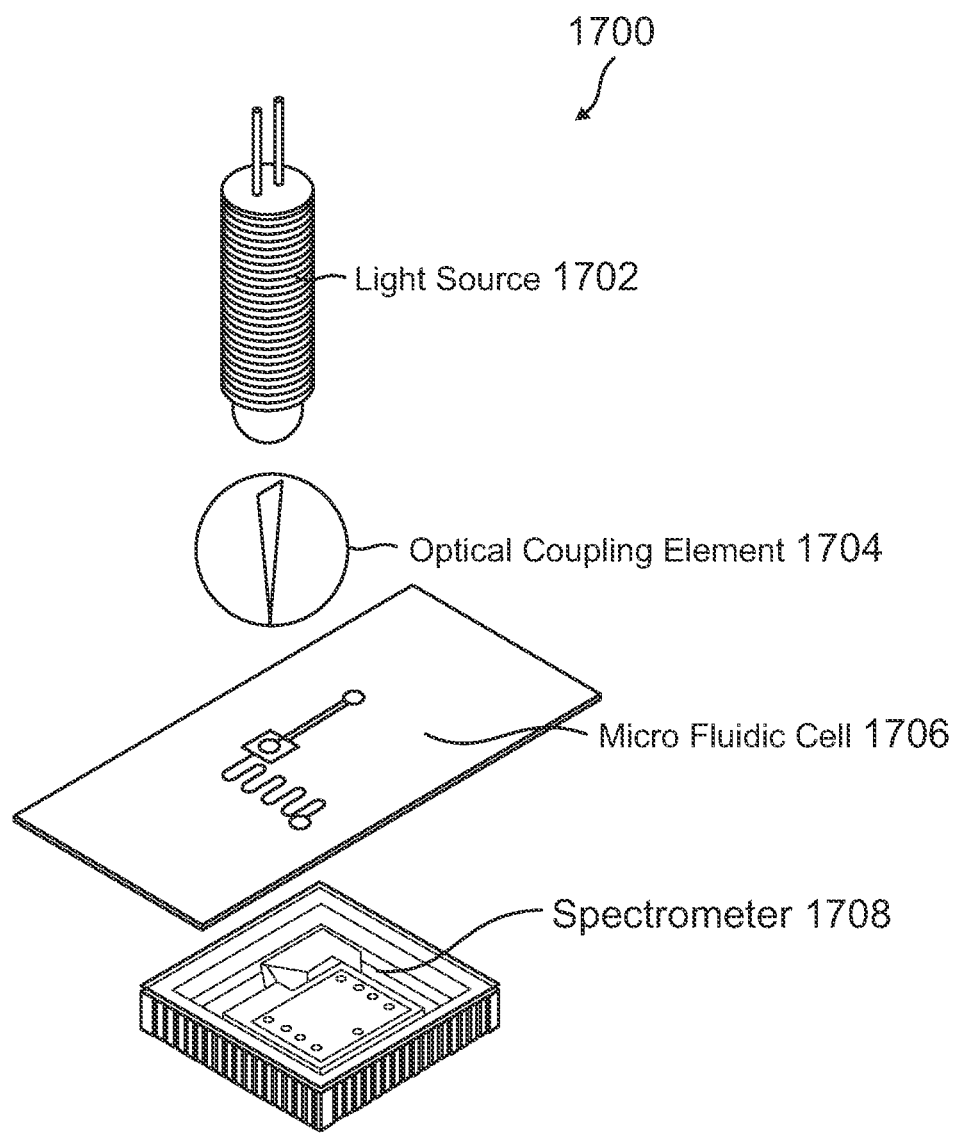
FIG. 17 is a diagram illustrating another example of an optical fluid analyzer according to some aspects.

FIG. 17 is a diagram illustrating another example of an optical fluid analyzer 1700 according to some aspects. The optical fluid analyzer 1700 includes a light source 1702, an optical coupling element 1704, a microfluidic cell 1706 configured to receive a fluid under test, and a spectrometer 1708. In the example shown in FIG. 17, the microfluidic cell 1706 is placed over the spectrometer 1708. Thus, the microfluidic cell 1706 can act as a transmission cell that includes optical windows configured to seal the microfluidic cell 1706 and pass light through the microfluidic cell. In addition, the light source 1702 with a compact form factor can be integrated above the microfluidic cell 1706.

Figure 18:
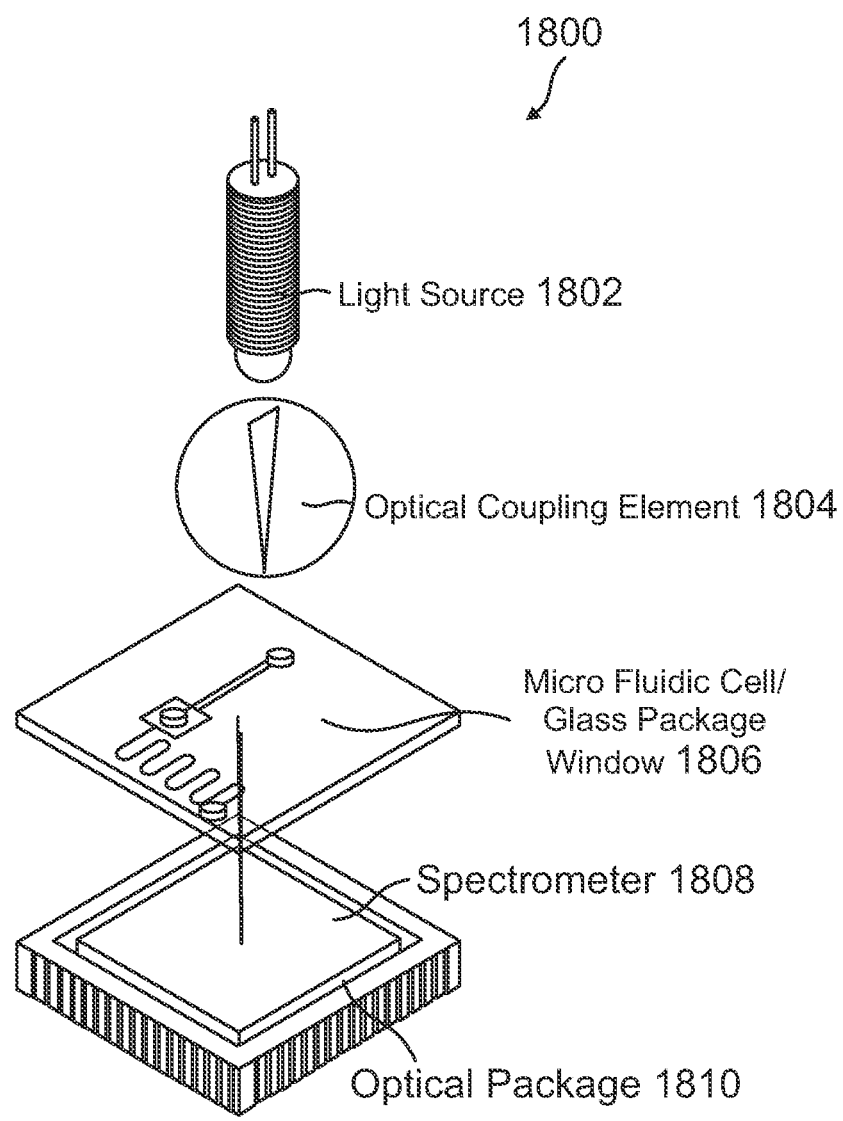
FIG. 18 is a diagram illustrating another example of an optical fluid analyzer according to some aspects.

FIG. 18 is a diagram illustrating another example of an optical fluid analyzer 1800 according to some aspects. The optical fluid analyzer includes a light source 1802, an optical coupling element 1804, a microfluidic cell 1806, and a spectrometer 1808. The spectrometer 1808 may be integrated into an optical package 1810. The microfluidic cell 1806 may further include optical windows configured to seal the microfluidic cell 1806 and to pass light through the microfluidic cell 1806. In addition, microfluidic cell 1806 may further act as a glass package window of the package 1810. Thus, the microfluidic cell/glass package window can be configured to seal the spectrometer 1808 (e.g., MEMS based FTIR spectrometer and detector). From an assembly point of view, the microfluidic cell 1806 can be on the same production line as the optical package for better assembly and production handling.

Figure 19:
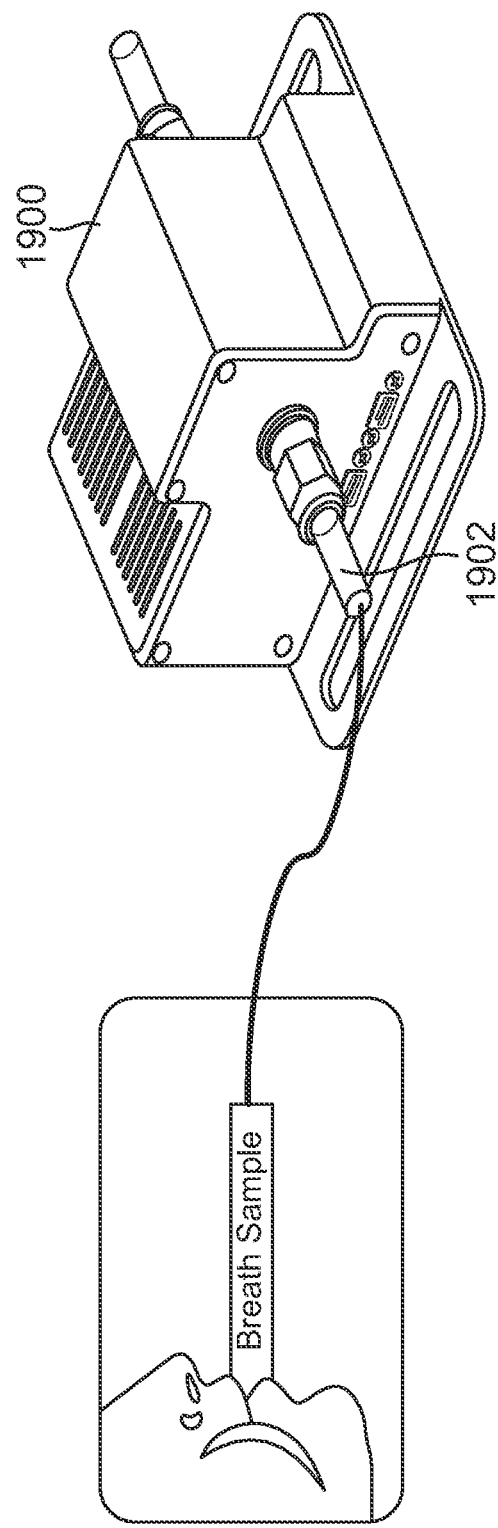
FIG. 19 is a diagram illustrating an example of optical fluid analyzer configured for viral detection according to some aspects.

FIG. 19 is a diagram illustrating an example of optical fluid analyzer 1900 configured for viral detection according to some aspects. In some examples, the optical fluid analyzer 1900 can be configured to measure the spectrum of a patient breath sample and predict the type of viral infection of the patient. For example, using different chemometric techniques, the ML engine (AI engine) of the optical fluid analyzer may predict the viral type from the absorption bands of the spectrum. To measure the breath sample, the optical fluid analyzer 1900 can include an input tube 1902 through which a patient can blow air from their mouth into the fluid cell of the optical fluid analyzer 1900.

The following provides an overview of examples of the present disclosure.

Example 1: An optical fluid analyzer, comprising: a light source configured to generate input light; a fluid cell configured to receive a fluid; a first optical element configured to seal the fluid cell on a first side thereof, the first optical element further configured to direct the input light into the fluid cell on the first side thereof; a second optical element configured to seal the fluid cell on a second side thereof opposite the first side, the second optical element further configured to receive output light from the fluid cell via the second side thereof; a spectrometer configured to receive the output light via the second optical element and to obtain a spectrum of the fluid based on the output light; and a machine learning engine configured to receive the spectrum and to generate a result defining at least one parameter of the fluid.

Example 2: The optical fluid analyzer of example 1, wherein the second optical element comprises: a flat optical window positioned between the fluid cell and the spectrometer and configured to seal the fluid cell on the second side thereof.

Example 3: The optical fluid analyzer of example 2, wherein the first optical element comprises: an additional flat optical window positioned between the light source and the fluid cell and configured to seal the fluid cell on the first side thereof.

Example 4: The optical fluid analyzer of example 3, further comprising: a ball lens coupled between the additional flat optical window and the fluid cell.

Example 5: The optical fluid analyzer of example 2, wherein the first optical element comprise a ball lens coupled between the light source and the first side of the fluid cell.

Example 6: The optical fluid analyzer of example 5, further comprising: ball seats configured to provide sealing between the ball lens and the first side of the fluid cell.

Example 7: The optical fluid analyzer of example 5 or 6, wherein the flat optical window comprises a package glass window of a package comprising the spectrometer, and further comprising: an O-ring configured to provide sealing between the package glass window and the second side of the fluid cell.

Example 8: The optical fluid analyzer of example 2, further comprising: a ball lens configured to direct the input light into the fluid cell on the first side thereof; and a rubber spacer or a spring coupled between the ball lens and the flat optical window.

Example 9: The optical fluid analyzer of any of examples 1 through 8, wherein the first optical element and the second optical element comprise an optical coupling element having a collimated design, the optical coupling element comprising: a first lens configured to couple the input light into the fluid cell on the first side thereof; and a second lens configured to receive the output light from the fluid cell via the second side thereof and to couple the output light into the spectrometer.

Example 10: The optical fluid analyzer of example 9, wherein each of the first lens and the second lens comprise ball lenses or half-ball lenses.

Example 11: The optical fluid analyzer of example 9, wherein each of the first lens and the second lens comprise Plano convex lenses and further comprising: a reflector coupled behind the light source and configured to collect back rays of the input light and to reflect the back rays towards the first lens.

Example 12: The optical fluid analyzer of any of examples 1 through 3, further comprising: a first off-axis parabolic mirror configured to receive the input light from the light source and to reflect the input light into the fluid cell on the first side thereof; and a second off-axis parabolic mirror configured to receive the output light from the fluid cell via the second side thereof and to reflect the output light into the spectrometer.

Example 13: The optical fluid analyzer of any of examples 1 through 3, further comprising: an off-axis parabolic mirror configured to receive the input light from the light source and to reflect the input light into the fluid cell on the first side thereof, wherein the second optical element comprises a lens configured to receive the output light from the fluid cell via the second side thereof and to direct the output light into the spectrometer.

Example 14: The optical fluid analyzer of any of examples 1, 2, or 5 through 9, wherein the first optical element comprises a ball lens coupled between the light source and the first side of the fluid cell, the ball lens being coated with a filter response coating on opposing ends thereof.

Example 15: The optical fluid analyzer of example 14, further comprising: a rotation device coupled to the ball lens and configured to rotate the ball lens between a first orientation in which the input light passes through the ball lens without passing through the filter response coating and a second orientation in which the input light passes through the filter response coating of the ball lens; wherein the optical fluid analyzer is configured to operate in a calibration mode to calibrate the machine learning engine when the ball lens is in the second orientation.

Example 16: The optical fluid analyzer of any of examples 1 through 15, further comprising: an actuator coupled to at least one of the first optical element or the second optical element and configured to cause motion of at least one of the first optical element or the second optical element to vary an optical path length in the fluid cell.

Example 17: The optical fluid analyzer of any of examples 1 through 16, wherein at least one of the first optical element or the second optical element comprises a coating on an internal side thereof facing the fluid cell to prevent stiction of the fluid.

Example 18: The optical fluid analyzer of any of examples 1 through 17, further comprising: a database comprising fluid data configured to train the machine learning engine.

Example 19: The optical fluid analyzer of any of examples 1 through 18, further comprising: at least one sensor configured to generate sensor data related to the fluid in the fluid cell and to provide the sensor data to the machine learning engine.

Example 20: The optical fluid analyzer of example 19, wherein the at least one sensor comprises at least one of a pressure sensor, a flow sensor, a temperature sensor, or a humidity sensor.

Example 21: The optical fluid analyzer of any of examples 1 through 20, wherein the fluid cell comprises a microfluidic cell.

Example 22: The optical fluid analyzer of example 21, wherein the second optical element comprises a package glass window of a package comprising the spectrometer, the package glass window comprising the microfluidic cell.

Example 23: The optical fluid analyzer of any of examples 1 through 22, wherein the fluid comprises a patient breath sample, and further comprising: an input tube coupled to the fluid cell and configured to receive the patient breath sample and to provide the patient breath sample into the fluid cell.

Example 24: The optical fluid analyzer of any of examples 1 through 23, wherein the spectrometer comprises a micro-electro-mechanical systems (MEMS) based Fourier Transform Infrared (FTIR) spectrometer.

Within the present disclosure, the word "exemplary" is used to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure.

One or more of the components, steps, features and/or functions illustrated in FIGS. 1-19 may be rearranged and/or combined into a single component, step, feature or function or embodied in several components, steps, or functions. Additional elements, components, steps, and/or functions may also be added without departing from novel features disclosed herein. The apparatus, devices, and/or components illustrated in FIGS. 1-19 may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. An optical fluid analyzer, comprising:
    a light source configured to generate input light;
    a fluid cell configured to receive a fluid;
    a first optical element configured to seal the fluid cell on a first side thereof, the first optical element further configured to direct the input light into the fluid cell on the first side thereof, wherein the first optical element comprises a ball lens coupled between the light source and the first side of the fluid cell, the ball lens being coated with a filter response coating on opposing ends thereof;
    a second optical element configured to seal the fluid cell on a second side thereof opposite the first side, the second optical element further configured to receive output light from the fluid cell via the second side thereof;
    a spectrometer configured to receive the output light via the second optical element and to obtain a spectrum of the fluid based on the output light;
    a rotation device coupled to the ball lens and configured to rotate the ball lens between a first orientation in which the input light passes through the ball lens without passing through the filter response coating and a second orientation in which the input light passes through the filter response coating of the ball lens; and
    a machine learning engine configured to receive the spectrum and to generate a result defining at least one parameter of the fluid, wherein the optical fluid analyzer is configured to operate in a calibration mode to calibrate the machine learning engine when the ball lens is in the second orientation.

2. The optical fluid analyzer of claim 1, wherein the second optical element comprises:
a flat optical window positioned between the fluid cell and the spectrometer and configured to seal the fluid cell on the second side thereof.

3. The optical fluid analyzer of claim 2, further comprising:
ball seats configured to provide sealing between the ball lens and the first side of the fluid cell.

4. The optical fluid analyzer of claim 2, wherein the flat optical window comprises a package glass window of a package comprising the spectrometer, and further comprising:
an O-ring configured to provide sealing between the package glass window and the second side of the fluid cell.

5. The optical fluid analyzer of claim 2, further comprising:
a rubber spacer or a spring coupled between the ball lens and the flat optical window.

6. The optical fluid analyzer of claim 1, wherein the first optical element and the second optical element comprise an optical coupling element, the optical coupling element comprising:
a first lens configured to couple the input light into the fluid cell on the first side thereof, the first lens comprising the ball lens; and
a second lens configured to receive the output light from the fluid cell via the second side thereof and to couple the output light into the spectrometer.

7. The optical fluid analyzer of claim 6, wherein the second lens comprises a ball lens.

8. The optical fluid analyzer of claim 1, further comprising:
a first off-axis parabolic mirror configured to receive the input light from the light source and to reflect the input light into the fluid cell on the first side thereof; and
a second off-axis parabolic mirror configured to receive the output light from the fluid cell via the second side thereof and to reflect the output light into the spectrometer.

9. The optical fluid analyzer of claim 1, further comprising:
an off-axis parabolic mirror configured to receive the input light from the light source and to reflect the input light into the fluid cell on the first side thereof, wherein the second optical element comprises a lens configured to receive the output light from the fluid cell via the second side thereof and to direct the output light into the spectrometer.

10. The optical fluid analyzer of claim 1, further comprising:
an actuator coupled to at least one of the first optical element or the second optical element and configured to cause motion of at least one of the first optical element or the second optical element to vary an optical path length in the fluid cell.

11. The optical fluid analyzer of claim 1, wherein at least one of the first optical element or the second optical element comprises a coating on an internal side thereof facing the fluid cell to prevent stiction of the fluid.

12. The optical fluid analyzer of claim 1, further comprising:
a database comprising fluid data configured to train the machine learning engine.

13. The optical fluid analyzer of claim 1, further comprising:
at least one sensor configured to generate sensor data related to the fluid in the fluid cell and to provide the sensor data to the machine learning engine.

14. The optical fluid analyzer of claim 13, wherein the at least one sensor comprises at least one of a pressure sensor, a flow sensor, a temperature sensor, or a humidity sensor.

15. The optical fluid analyzer of claim 1, wherein the fluid cell comprises a microfluidic cell.

16. The optical fluid analyzer of claim 15, wherein the second optical element comprises a package glass window of a package comprising the spectrometer, the package glass window comprising the microfluidic cell.

17. The optical fluid analyzer of claim 1, wherein the fluid comprises a patient breath sample, and further comprising:
an input tube coupled to the fluid cell and configured to receive the patient breath sample and to provide the patient breath sample into the fluid cell.

18. The optical fluid analyzer of claim 1, wherein the spectrometer comprises a micro-electro-mechanical systems (MEMS) based Fourier Transform Infrared (FTIR) spectrometer.

19. The optical fluid analyzer of claim 2, further comprising:
a flat optical window positioned between the light source and the fluid cell and configured to seal the fluid cell on the first side thereof, the ball lens being coupled between the flat optical window and the fluid cell.

* * * * *